United States Patent [19]

Sprague

[11] 4,303,662
[45] Dec. 1, 1981

[54] CARBOXYACYL, MERCAPTO AND ACYLMERCAPTO DERIVATIVES OF HETEROBICYCLO COMPOUNDS

[75] Inventor: Peter W. Sprague, Pennington, N.J.

[73] Assignee: E. R. Squibb & Sons, Inc., Princeton, N.J.

[21] Appl. No.: 209,780

[22] Filed: Nov. 24, 1980

[51] Int. Cl.³ .................. A61K 31/435; A61K 31/40; C07D 491/08
[52] U.S. Cl. .................. 424/256; 424/274; 260/326.25; 260/326.32; 546/113
[58] Field of Search ............ 260/326.32, 326.25; 546/113; 424/274, 256

[56] References Cited

U.S. PATENT DOCUMENTS

| | | | |
|---|---|---|---|
| 4,052,511 | 10/1977 | Cushman et al. | 424/274 |
| 4,105,776 | 8/1978 | Ondetti et al. | 424/274 |
| 4,154,935 | 5/1979 | Ondetti et al. | 546/189 |

Primary Examiner—Henry R. Jiles
Assistant Examiner—Jane T. Fan
Attorney, Agent, or Firm—Lawrence S. Levinson; Stephen B. Davis

[57] ABSTRACT

A compound of the formula

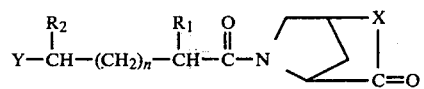

wherein $R_1$ is hydrogen, lower alkyl, phenyl lower alkyl or halo substituted lower alkyl;
$R_2$ is hydrogen, lower alkyl, phenyl lower alkyl or halo substituted lower alkyl;
n is 0, 1 or 2;
X is —$(CH_2)_mZ$—;
Z is oxygen, sulfur or imino;
m is 0 or 1;
Y is S-R or

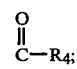

R is hydrogen, lower alkyl,

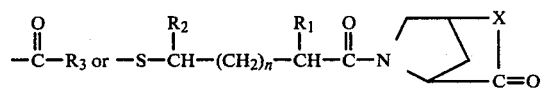

$R_3$ is lower alkyl, phenyl or phenyl lower alkyl;
and $R_4$ is hydroxy, amino, hydroxyamino or lower alkoxy. These compounds are useful as hypotensive agents.

15 Claims, No Drawings

CARBOXYACYL, MERCAPTO AND ACYLMERCAPTO DERIVATIVES OF HETEROBICYCLO COMPOUNDS

BACKGROUND OF THE INVENTION

Cushman, et al. in U.S. Pat. No. 4,052,511 discloses angiotensin converting enzyme inhibitors of the formula

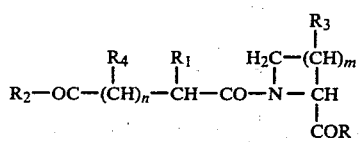

wherein $R_1$ and $R_4$ each is hydrogen, lower alkyl or phenyl lower alkyl;
$R_2$ is hydroxy, amino, hydroxyamino or lower alkoxy; and n is 0 to 2.

Ondetti, et al. in U.S. Pat. No. 4,154,935 discloses hyportensive agents of the formula

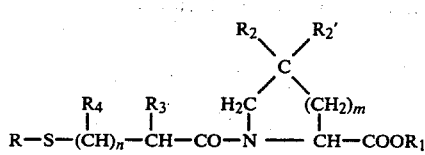

wherein R is hydrogen, lower alkanoyl or

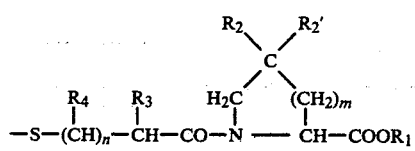

$R_3$ and $R_4$ is each hydrogen, lower alkyl or trifluoromethyl; and n is 0 or 1.

Ondetti, et al. in U.S. Pat. No. 4,105,776 disclose angiotensin converting enzyme inhibitors of the formula

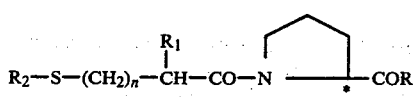

wherein
$R_1$ is hydrogen or lower alkyl;
$R_2$ is hydrogen, $R_5$-CO—, $R_6$-S— or $R_7$;
$R_5$ is lower alkyl;
$R_6$ is lower alkyl
n is 0, 1 or 2;
and $R_7$ is

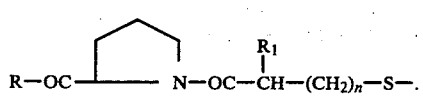

SUMMARY OF THE INVENTION

This invention provides new compounds of the formula

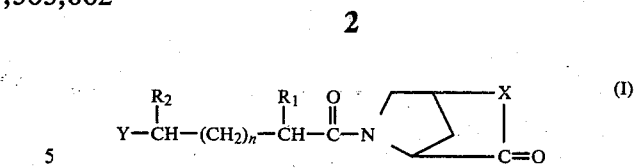

wherein
$R_1$ is hydrogen, lower alkyl, phenyl lower alkyl or halo substituted lower alkyl;
$R_2$ is hydrogen, lower alkyl, phenyl lower alkyl or halo substituted lower alkyl;
n is 0, 1 or 2;
X is —$(CH_2)_mZ$—;
Z is oxygen, sulfur or imino;
m is 0 or 1;
Y is —S—R or

R is hydrogen, lower alkyl,

 or

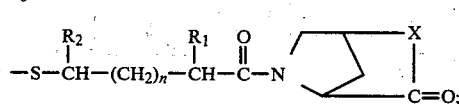

$R_3$ is lower alkyl, phenyl or phenyl lower alkyl; and $R_4$ is hydroxy, amino, hydroxyamino or lower alkoxy.

DETAILED DESCRIPTION OF THE INVENTION

The invention in its broadest aspect relates to carboxyacyl, mercapto and acylmercapto derivatives of heterobicyclo compounds having formula I above to compositions containing such compounds and to the method for using such compounds as anti-hypertensive agents.

The lower alkyl groups represented by any of the variables include straight and branched chain hydrocarbon radicals from methyl to heptyl, for example, methyl, ethyl, propyl, isopropyl, butyl, isobutyl, t-butyl, pentyl, isopentyl and the like. The $C_1$–$C_4$ members and especially the $C_1$ and $C_2$ members, are preferred.

The term lower alkoxy includes such lower alkyl groups bonded through an oxygen.

The term phenyl-lower alkyl includes a phenyl ring attached to a lower alkyl group as defined above. Phenylmethyl and phenylethyl are preferred.

The halogens are chlorine, bromine and fluorine; chlorine and fluorine being preferred.

The term halo substituted lower alkyl represents a lower alkyl group wherein at least one hydrogen has been replaced by a halogen. Trifluoromethyl is preferred.

The compounds of formula I wherein Z is oxygen or sulfur and $R_3$ is lower alkyl can be prepared by coupling a compound of the formula

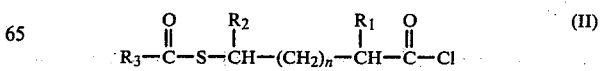

with an acid halogen salt compound of the formula

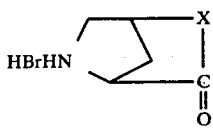

Compounds of formula III may be prepared by treating a compound of the formula

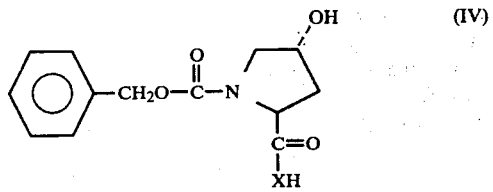

with triphenylphosphine, diethylazodicarboxylate and tetrahydrofuran to form a compound of the formula

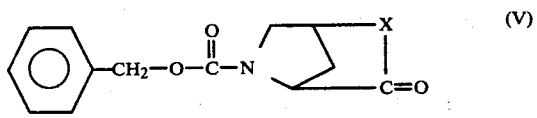

and then treating the compound of formula V with acetic acid and hydrogen bromide to form the compound of formula III.

The compounds of formula I wherein Z is imino and $R_3$ is lower alkyl can be prepared by coupling a compound of the formula

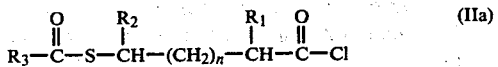

with a compound of the formula

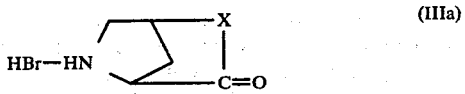

Compounds of formula IIIa may be prepared by treating a compound of the formula

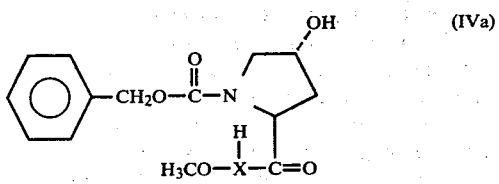

with triphenylphosphine, and diethylazodicarboxylate to form a compound of the formula

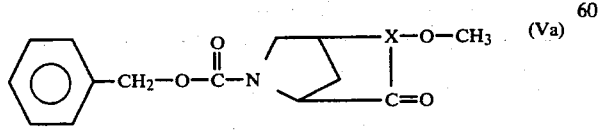

and then treating the compound of formula Va with liquid ammonia containing sodium to form the compound of formula IIIa.

The compounds of formula I wherein $R_4$ is lower alkoxy and Z is oxygen, sulfur or imino, can be prepared by coupling a compound of the formula

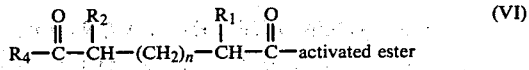

with a compound of the formula

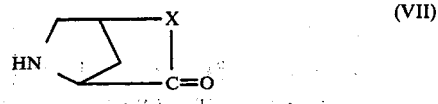

The compounds of formula VI can be prepared by treating a compound of the formula

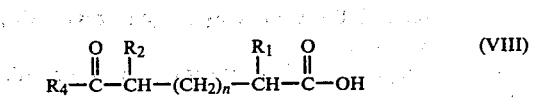

with dicyclohexylcarbodiimide.

The compounds of formula VII can be obtained by treating compounds of the formula

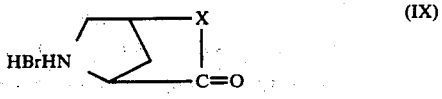

with sodium bicarbonate.

The compounds of formula

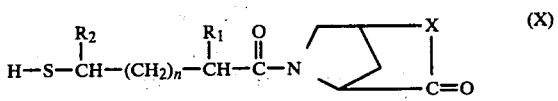

which are formula I compounds wherein R is hydrogen, are produced from compounds of formula I wherein R is

by ammonolysis, e.g., treatment with aqueous alcoholic ammonia or treatment with trifluoroacetic acid.

The compounds of formula I wherein Z is oxygen, sulfur or imino and R is lower alkyl are produced by reacting a compound of formula X with the corresponding halide of the formula R-halide.  (XI)

In the particular case wherein R is

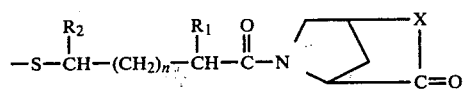

$R_1$, $R_2$, n and X are the same as the corresponding substituents in formula I, the symmetrical disulfides can be obtained by direct oxidation of a compound of formula X with iodine.

The compounds of formula

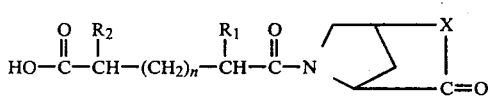

which are formula I compounds wherein $R_4$ is hydroxy are produced by coupling a compound of formula VII with a compound of formula XIIa

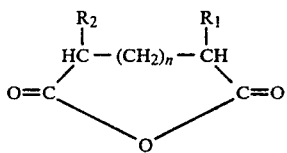

followed by chromatographic separation of the isomers produced.

The compounds of the formula

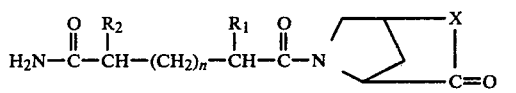

are Formula I compounds wherein $R_4$ is amino and are produced by combination of compounds of Formula VII with a compound of Formula XIIIa

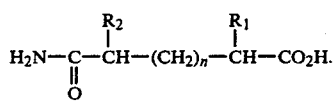

If a compound of the Formula

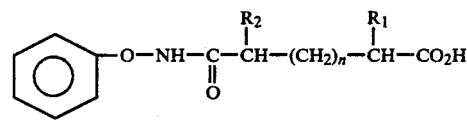

is substituted for a compound of Formula XIIIa and the product of the reaction is debenzylated by catalytic hydrogenation then compounds of Formula

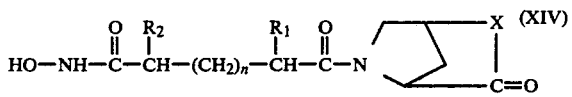

which are Formula I compounds wherein $R_4$ is hydroxyamino, are produced.

Preferred compounds of the invention are those wherein
Y is S—R;
R is

$R_3$ is lower alkyl;
$R_2$ is phenyl lower alkyl or hydrogen;
$R_1$ is lower alkyl;
n is 1;
m is 0; and Z is oxygen.

wherein Y is S—R;
R is hydrogen;
$R_2$ is phenyl lower alkyl or hydrogen;
$R_1$ is lower alkyl;
n is 1; m is 0; and Z is oxygen.

wherein Y is S—R;
R is hydrogen;
$R_2$ is phenyl lower alkyl or hydrogen;
$R_1$ is lower alkyl;
n is 0;
m is 0;
and Z is oxygen.

wherein

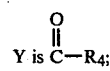

$R_4$ is lower alkoxy;
$R_2$ is phenyl lower alkyl or hydrogen;
$R_1$ is lower alkyl;
n is 1;
m is 0;
and Z is oxygen.

wherein Y is S—R;

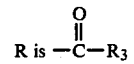

$R_3$ is lower alkyl;
$R_2$ is phenyl lower alkyl or hydrogen;
$R_1$ is lower alkyl;
n is 0;
m is 0;
and Z is oxygen.

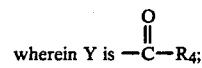

$R_4$ is lower alkoxy;
$R_2$ is phenyl lower alkyl or hydrogen;
$R_1$ is lower alkyl;
n is 0;
m is 0;
and Z is oxygen.

Most preferred compounds of formula I are those wherein $R_1$ is methyl,
n is zero and $R_2$ is hydrogen,
and wherein $R_1$ is methyl,
n is one and $R_2$ is hydrogen.

Most preferred compounds of formula I are those wherein $R_1$ is methyl, n is one and $R_2$ is phenylethyl;
and wherein $R_1$ is methyl, n is one and $R_2$ is hydrogen.

The compounds of formula I are useful as hypotensive agents. They inhibit the conversion of the decapeptide angiotensin I to angiotensin II and, therefore, are useful in relieving angiotensin related hypertension. The action of the enzyme renin on angiotensin, a pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., rats and dogs. The compounds of this invention intervene in the angiotensinogen→(renin)→angiotensin I→(ACE)→angiotensin II sequence by inhibiting angiotensin converting enzyme and reducing or eliminating the formation of the pressor substance angiotensin II. Thus by the administration of a composition containing one, or a combination of compounds, of formula I angiotensin dependent hypertension in the species of mammal suffering therefrom is alleviated. A single dose, or preferably two to four divided daily doses, provided on a basis of about 0.1 to 100 mg. per kilogram of body weight per day, preferably about 1 to 15 mg per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises (for a 70 kg mammal) a total daily dosage of about 30 to 600 mg, preferably about 30 to 300 mg, of a compound of this invention, and about 15 to 300 mg, preferably about 15 to 200 mg of the diuretic, to a mammalian species in need thereof. Exemplary of the diuretics contemplated for use in combination with a compound of this invention are the thiazide diuretics, e.g. chlorthiazide, hydrochlorothiazide, flumethiazide, hydroglumethiazide, bendroflumethiazide, methclothiazide, trichlorothiazide, polythiazide or benthiazide, as well as ethacrynic acid, ticrynafen, chlorthalidone, furosemide, musolimine, bumetanide, triamterene, amiloride and spironolactone, and salts of such compounds.

The compounds of formula I can be formulated for use in the reduction of blood pressure in compositions such as tablets, capsules or elixirs for oral administration or in sterile solutions or suspensions for parenteral administration. About 10 to 500 mg of a compound of mixture of compounds of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrated process details are set forth in the following examples for the various reactions. These examples are preferred embodiments and also serve as models for the preparation of other compounds of this invention. The temperatures are given in degrees on the centigrade scale.

EXAMPLE 1

[1R-[1α,5(S*)]]-Ethanethioic acid, 2-methyl-3-oxo-3-(3-oxo-2-oxa-5-azabicyclo[2.2.1]hept-5-yl)propyl S-ester.

(a) N-Carbobenzyloxy-cis-4-Hydroxy-L-proline lactone

To a solution of 10.0 g (0.0733 mol) of N-carbobenzyloxy-trans-4-hydroxy-L-proline, 14.5 g (1.5 eq) of triphenylphosphine in 300 ml of dry (sieve) tetrahydrofuran (THF) is added 9.8 g (1.5 eq) of diethylazo-dicarboxylate (DEAD) dropwise over 2-3 hr at room temperature. A precipitate formed on the addition of each drop and the rate of addition is adjusted so that the precipitate redissolved before the next drop is added. After stirring overnight at room temperature, the solvent is removed under vacuum and the residue slurried with 200 ml of ether. The mixture is filtered to remove the insoluble triphenyl phosphineoxide and diethylazodicarboxylate. The filtrate is stripped and chromatographed on silica gel with ether:pentane (1:1) with the new spot ($R_f$; 0.5 silica gel, ether, blue-gray with vanillin & heat) being collected—yield: 5.5 g (59%).

(b) cis-4-Hydroxy-L-proline lactone HBr salt (Ref. J.A.C.S., 79, 185 (1957))

2.3 g (0.0087 mol) of N-carbobenzyloxy-cis-4-hydroxy-L-proline lactone is dissolved in 10 ml of 30% HBr in acetic acid; the product precipitated from the reaction mixture. After 1 hour the mixture is centrifuged and the supernatant decanted. The product is washed with 10 ml of fresh acetic acid and centrifuged. The pellet is washed with 50 ml of ether, filtered off and dried under vacuum to yield 1.45 g (86%) cis-4-hydroxy-L-proline lactone HBr salt m.p. 199°–201° (lit. 193°–194°).

Analysis calc'd for $C_5H_7NO_2 \cdot HBr$: C, 29.58; H, 4.46; N, 6.90; Br, 39.47; Found: C, 29.75; H, 4.19; N, 6.86; Br, 39.75.

(c) [1R-[1α,4α,5(S*)]]-Ethanethioic acid, 2-methyl-3-oxo-3-(3-oxo-2-oxa-5-azabicyclo[2.2.1]hept-5-yl)propyl S-ester.

To 1.6 g (0.0088 mol) of cis-4-hydroxy-L-proline lactone HBr salt suspended in 30 ml of dry (sieve) tetrahydrofuran (THF) is added 1.7 g (0.02 mol) of pyridine and 3.2 g (0.017 mol) of (S)-3-acetylthio-2-methylpropionyl chloride all at once. After stirring at room temperature for 2 hours the mixture is filtered, the filtrate evaporated to dryness and triturated with ether. The ether insoluble material (1.0 g m.p. 96°–102°) is recrystallized from 15 ml of ethylacetate to yield 750 mg (33%) of [1R-[1α,4α,5(S*)-]]-ethanethioic acid, 2-methyl-3-oxo-3-(3-oxo-2-oxa-5-azabicyclo[2.2.1]hept-5-yl)propyl S-ester m.p. 111°–112°.

Analysis calc'd for $C_{11}H_{15}NO_4S$: C, 51.36; H, 5.88; N, Found: C, 51.08; H, 5.89; N, 5.27; S, 12.31.

EXAMPLE 2

β-Methyl-γ,3-dioxo-2-oxa-5-azabicyclo[2.2.1]heptane-5-butanoic acid, methyl ester.

(a) cis-4-hydroxy-L-proline lactone cis-4-hydroxy-L-proline lactone HBr salt made as in Example 1 (b) is added to aqueous sodium bicarbonate 10% solution. Then extracted with ethyl acetate (commercial grade). The solvent is then stripped by warming under vacuum. The residue is cis-4-hydroxy-L-proline lactone.

(b) 3-Methoxycarbonyl-2-R-methylpropionic acid (RS)-3-methoxycarbonyl-2-methylpropionic acid (36.8 g) is dissolved in ether (200 ml) and mixed with dehydroabietylamine (91.3 g) dissolved in 400 ml of ether. After storing the mixture for one hour at room temperature the crystals are filtered and recrystallized from ethyl acetate to yield 25.2 g of 3-methoxycarbonyl-2-R-methylpropionic acid having a melting point of (173°) 144°–146° C. $[\alpha]^{22} = +30.5°$ c=1.5, ethanol).

(c) β-Methyl-γ,3-dioxo-2-oxa-5-azabicyclo[2.2.1]heptane-5-butanoic acid, methyl ester.

3-methoxycarbonyl-2-R-methylpropionic acid (2 g, 13.75 mmoles) and N-hydroxybenzotriazole (1.91 g, 12.5 mmoles) are dissolved in tetrahydrofuran (36 ml) and to this solution, chilled in an ice bath, dicyclohexylcarbodiimide (2.57 g, 12.5 mmoles) is added. After two hours stirring at room temperature the precipitate is filtered off and the filtrate is dissolved in N,N-dimethylformamide (36 ml) and cis-4-hydroxy-L-proline lactone (3.8 g, 12.5 mmoles) and triethylamine (3.5 ml) are added. The reaction is allowed to proceed for eighteen hours at room temperature, the solvent is removed in vacuo, the residue is dissolved in ethyl acetate and washed with 0.1 N HCl, saturated aqueous sodium chloride, dried (MgSO$_4$) and concentrated to dryness. The residue is then taken into ethyl acetate, the crystals are filtered off and the filtrate concentrated to dryness and chromatographed on a column of silica gel with benzene:acetic acid (8:2). The fractions containing the desired product are lyophilized and the residue crystallized from ethyl acetate-hexane to yield 3.3 g, β-methyl-γ,3-dioxo-2-oxa-5-azabicyclo[2.2.1]heptane-5-butanoic acid, methyl ester.

EXAMPLE 3

γ-Methyl-δ,3-dioxo-α-(2-phenylethyl)-2-oxa-5-azabicyclo[2.2.1]heptane-5-pentanoic acid, methyl ester.

(a) 4-Methoxycarbonyl-6-phenyl-2-R-methylhexanoic acid

4-Methoxycarbonyl-2-R-methylbutyric acid (46 g, 10 mmoles) is added to a one molar solution of lithium diisopropylamide in tetrahydrofuran (20 ml) chilled at −78°. The enolate is allowed to form for forty minutes at −78°. Phenethylbromide (185 g, 10 mmole) is added and the reaction mixture is allowed to reach 4° C. and maintained at this temperature until the reaction is complete as monitored by tlc. The reaction mixture is diluted with ethyl acetate and washed with 10% aqueous bisulfate and water. The organic layer is dried (MgSO$_4$) and concentrated to dryness to give 4-methoxycarbonyl-6-phenyl-2-R-methylhexanoic acid.

(b) γ-Methyl-δ,3-dioxo-α-(2-phenylethyl)-2-oxa-5-azabicyclo[2.2.1]heptane-5-pentanoic acid, methyl ester By following the procedure of Example 2 but substituting 4-methoxycarbonyl-6-phenyl-2-R-methylhexanoic acid for 3-methoxycarbonyl-2-R-methylpropionic acid in part (c) then γ-methyl-δ,3-dioxo-α-(2-phenylethyl)-2-oxa-5-azabicyclo[2.2.1]heptane-5-pentanoic acid, methyl ester is formed.

EXAMPLE 4

[1S-[1α,4α,5(S*)]]-5-[3-(Acetylthio)-2-methyl-1-oxopropyl]-2,5-diazabicyclo[2.2.1]heptan-3-one (a) Methyl N-benzoyloxycarbonyl-4-trans-hydroxyproline hydroxamate A solution of N-benzoyloxycarbonyl-4-transhydroxyproline (2.65 g, 10 mmole) and dry, distilled, triethylamine (1.05 g, 10 mmole) in tetrahydrofuran (THF) (500 ml) is cooled to −15° with stirring and a solution of ethylchloroformate (1.40 g, 10 mmole) in tetrahydrofuran (100 ml) is added dropwise as the temperature is maintained at −15° C. Following the addition the mixture is stirred at −15° C. for 30 minutes and then warmed to 0°. A solution of methoxylamine (0.94 g, 20 mmole) in tetrahydrofuran (20 ml) is added and the reaction stirred at 0° an additional 3 hours. The mixture is acidified with concentrated HCl to pH 2 and extracted with ethylacetate. Concentration of the extracts gives the methyl hydroxamate which is purified by chromatography on silica gel to yield 2.00 g 70% of methyl N-benzyloxycarbonyl-4-trans-hydroxy proline hydroxamate.

(b) (1S-[1α,4α))-2-methoxy-5-benzoyloxycarbonyl-2,5-diazabicyclo[2.2.1]heptan-3-one Diethyldiazodicarboxylate (1.74 g, 10 mmole) is added dropwise to a solution of methyl N-benzyloxycarbonyl-4-trans-hydroxyproline (2.94 g, 10 mmole) and triphenylphosphine (2.62 g, 10 mmole) in methylenechloride (100 ml) and the resulting mixture stirred at room temperature for 2 hours. The solvent is removed under vacuum and the residue chromatographed on silica gel yielding 1.6 g of (1S(1α,4α))-2-methoxy-5-benzoyl oxycarbonyl-2,5-diazabicyclo[2.2.1]heptan-3-one.

(c) (1S-(1α,4α))-2,5-diazabicyclo[2.2.1]heptan-3-one (1S-[1α,4α))-2-methoxy-5-benzoyloxycarbonyl-2,5-diazabicyclo[2.2.1]heptan-3-one (1.6 g, 5.8 mmole) in tetrahydrofuran (20 ml) is added dropwise to a mixture of liquid ammonia containing 2 equivalents of sodium (266 mg) at −78°. After 15 minutes the reaction is quenched by addition of excess ammonium chloride. The ammonia is removed and the residue extracted with tetrahydrofuran (THF). The extracts are concentrated to yield 0.5 g of (1S-(1α,4α))-2,5-diazabicyclo[2.2.0-]heptan-3-one.

(d) [1S-[1α,4α,5(S*)]]-5-[3-(Acetylthio)-2-methyl-1-oxo propyl]-2,5-diazabicyclo[2.2.0]heptan-3-one By following the procedure of Example 1(c) but substituting (1S-(1α,4α)-2,5-diazabicyclo[2.2.1]heptan-3-one in place of cis-4-hydroxy-L-proline lactone HBr salt then [1S-[1α,4α,5(S*)]]-5-[3-(acetylthio)-2-methyl-1-oxopropyl]-2,5-diazabicyclo[2.2.1]-heptan-3-one is obtained.

EXAMPLE 5

[1S-[1α,4α,5(S*)]]-5-[3-(Acetylthio)-2-methyl-1-oxopropyl]-2-thia-5-azabicyclo[2.2.1]heptan-3-one By following the procedure of Example 1 but substituting (trans)-4-hydroxy-1-[(phenylmethoxy)-carbonyl]-L-proline thio acid in place of N-carbobenzyloxytrans-4-hydroxy-L-proline then [1S-[1α,4α,5(S*)]]-5-[3-(acetylthio)-2-methyl-1-oxopropyl]-2-thia-5-azabicyclo[2.2.1]heptan-3-one is obtained.

EXAMPLES 6–42

By following the procedure of Example 1 but substituting a compound of Column I in place of N-carbobenzyloxy trans 4-hydroxy-L-proline in part (a) and a compound of Column II in place of (S)-3-acetylthio-2-methylpropionyl chloride in part (b) a compound of Column III is obtained.

Column I

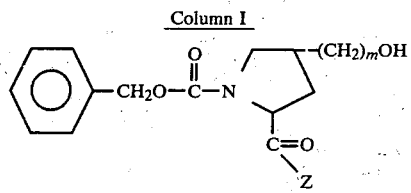

wherein Z is O or S

Column II

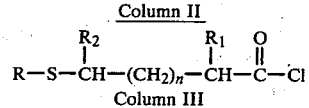

Column III

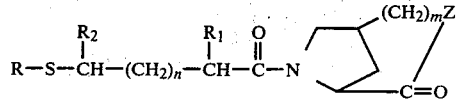

| Example | Z | R | R₁ | R₂ | n | m |
|---|---|---|---|---|---|---|
| 6a | —O— | —C(=O)—CH₃ | —H | —(CH₂)₂—C₆H₅ | 1 | 0 |
| 6 | —O— | —C(=O)—C₆H₅ | —H | —(CH₂)₂—C₆H₅ | 1 | 0 |
| 7 | —O— | —C(=O)—CH₂—C₆H₅ | —H | —(CH₂)₂—C₆H₅ | 1 | 0 |
| 8 | —O— | —C(=O)—CH₃ | —H | —CH₂—C₆H₅ | 1 | 0 |
| 9 | —O— | —C(=O)—C₆H₅ | —H | —CH₂—C₆H₅ | 1 | 0 |
| 10 | —O— | —C(=O)—CH₂—C₆H₅ | —H | —CH₂—C₆H₅ | 1 | 0 |
| 11 | —S— | —C(=O)—CH₃ | —H | —(CH₂)₂—C₆H₅ | 1 | 0 |
| 12 | —S— | —C(=O)—C₆H₅ | —H | —(CH₂)₂—C₆H₅ | 1 | 0 |
| 13 | —S— | —C(=O)—CH₂—C₆H₅ | —H | —(CH₂)₂—C₆H₅ | 1 | 0 |
| 14 | —S— | —C(=O)—CH₂—C₆H₅ | —H | —(CH₂)₂—C₆H₅ | 2 | 0 |
| 15 | —O— | —C(=O)—CH₃ | —CH₃ | —(CH₂)₂—C₆H₅ | 1 | 0 |
| 16 | —O— | —C(=O)—C₆H₅ | —CH₃ | —(CH₂)₂—C₆H₅ | 1 | 0 |
| 17 | —O— | —C(=O)—CH₂—C₆H₅ | —CH₃ | —(CH₂)₂—C₆H₅ | 1 | 0 |
| 18 | —O— | —C(=O)—CH₃ | —CH₃ | —CH₂—C₆H₅ | 1 | 0 |
| 19 | —O— | —C(=O)—C₆H₅ | —CH₃ | —CH₂—C₆H₅ | 1 | 0 |
| 20 | —O— | —C(=O)—CH₂—C₆H₅ | —CH₃ | —CH₂—C₆H₅ | 1 | 0 |
| 21 | —S— | —C(=O)—CH₃ | —CH₃ | —(CH₂)₂—C₆H₅ | 1 | 0 |
| 22 | —S— | —C(=O)—C₆H₅ | —CH₃ | —(CH₂)₂—C₆H₅ | 1 | 0 |
| 23 | —S— | —C(=O)—CH₂—C₆H₅ | —CH₃ | —(CH₂)₂—C₆H₅ | 1 | 0 |
| 24 | —O— | —C(=O)—CH₃ | —H | —H | 1 | 0 |
| 25 | —O— | —C(=O)—C₆H₅ | —H | —H | 1 | 0 |
| 26 | —O— | —C(=O)—CH₂—C₆H₅ | —H | —H | 1 | 0 |
| 27 | —O— | —C(=O)—CH₂—C₆H₅ | —H | —H | 0 | 0 |
| 28 | —O— | —C(=O)—CH₃ | —H | —CH₂Cl | 1 | 0 |

-continued

| Example | Z | R | R₁ | R₂ | n | m |
|---|---|---|---|---|---|---|
| 29 | —O— | —C(=O)—C₆H₅ | —H | —CH₂Cl | 1 | 0 |
| 30 | —O— | —C(=O)—CH₂—C₆H₅ | —H | —CH₂Cl | 1 | 0 |
| 31 | —S— | —C(=O)—CH₃ | —H | —H | 0 | 1 |
| 32 | —S— | —C(=O)—C₆H₅ | —H | —H | 1 | 1 |
| 33 | —S— | —C(=O)—CH₂—C₆H₅ | —H | —H | 2 | 1 |
| 34 | —O— | —C₃H₇ | —H | —(CH₂)₂—C₆H₅ | 1 | 0 |
| 35 | —O— | —CH₃ | —H | —(CH₂)₂—C₆H₅ | 1 | 0 |
| 36 | —O— | —C₂H₅ | —H | —(CH₂)₂—C₆H₅ | 1 | 0 |
| 37 | —O— | —C₃H₇ | —H | —CH₂—C₆H₅ | 1 | 0 |
| 38 | —O— | —CH₃ | —H | —CH₂—C₆H₅ | 1 | 0 |
| 39 | —O— | —C₂H₅ | —H | —CH₂—C₆H₅ | 1 | 0 |
| 40 | —S— | —C₃H₇ | —H | —(CH₂)₂—C₆H₅ | 1 | 0 |
| 41 | —S— | —CH₃ | —H | —(CH₂)₂—C₆H₅ | 1 | 0 |
| 42 | —S— | —C₂H₅ | —H | —(CH₂)₂—C₆H₅ | 1 | 0 |

EXAMPLES 43-51

By following the procedure of Example 2 but substituting the compound of Column I in place of cis-4-hydroxy-L-proline lactone HBr salt in part (a) and a compound of Column II in place of 3-methoxycarbonyl-2-R-methylpropionic acid in part (c) a compound of Column III is obtained.

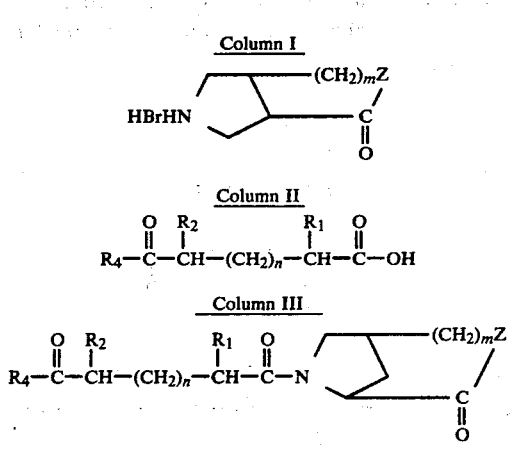

| Example | Z | R₁ | R₂ | R₄ | n | m |
|---|---|---|---|---|---|---|
| 43 | —O— | —CH₃ | —(CH₂)₂—C₆H₅ | —O—CH₃ | 1 | 1 |
| 44 | —O— | —H | —(CH₂)₂—C₆H₅ | —O—C₂H₅ | 1 | 0 |
| 45 | —O— | —CH₃ | —(CH₂)₂—C₆H₅ | —O—C₂H₅ | 1 | 0 |
| 46 | —NH— | —CH₃ | —(CH₂)₂—C₆H₅ | —O—CH₃ | 1 | 0 |
| 47 | —NH— | —H | —(CH₂)₂—C₆H₅ | —O—C₂H₅ | 1 | 0 |
| 48 | —NH— | —CH₃ | —(CH₂)₂—C₆H₅ | —O—C₂H₅ | 1 | 0 |
| 49 | —S— | —CH₃ | —(CH₂)₂—C₆H₅ | —O—CH₃ | 1 | 0 |
| 50 | —S— | —H | —(CH₂)₂—C₆H₅ | —O—C₂H₅ | 1 | 0 |

-continued

| Example | Z | R1 | R2 | R4 | n | m |
|---|---|---|---|---|---|---|
| 51 | —S— | —CH3 | —(CH2)2—⟨O⟩ | —O—C2H5 | 1 | 0 |

EXAMPLE 52

β-Methyl-γ,3-dioxo-2-oxa-5-azabicyclo[2.2.1]heptane-5-butanoic acid, amide

A mixture of 3-carboxybutanoic acid amide (1.3 g, 10 mmole), and carbonyl diimidazole (1.62 g, 10 mmole) in acetonitrile is stirred under argon at 0° for 1 hour. The mixture is treated with triethylamine (2.0 g, 20 mmole) and cis-4-hydroxyproline lactone hydrobromide (2.1 g, 10 mmole) and after 5 hours the acetonitrile is removed under vacuum and the residue positioned between ethylacetate and 1. N HCl. The organic phase is washed with brine, dried (MgSO4) and the solvent removed under vacuum to give β-methyl-γ,3-dioxo-2-oxa-5-azabicyclo[2.2.1]heptane-5-butanoic acid, amide.

EXAMPLE 53

β-Methyl-γ,3-dioxo-2-oxa-5-azabicyclo[2.2.1]heptane-5-butanoic acid hydroxamide

A mixture of 3-carboxybutanoic acid O-benzyl hydroxamide (2.1 g, 10 mmole) and carbonyl diimidazole (1.62 g, 10 mmole) in acetonitrile is stirred under argon at 0° for 1 hour. The mixture is treated with triethylamine (2.0 g, 20 mmole) and cis-4-hydroxyproline lactone hydrobromide (2.1 g, 10 mmole) and after 5 hours the acetonitrile is removed under vacuum and the residue partitioned between ethylacetate and 1 N HCl. The organic layer is separated, dried (MgSO4) and condensed under vacuum to yield the O-benzyl derivative of β-methyl-γ,3-dioxo-2-oxa-5-azabicyclo[2.2.1]-heptane-5-butanoic acid hydroxamide. The benzyl group is removed by treatment of this substance in ethanol containing 100 mg of 10% Pd/C with hydrogen until 1 mole of gas has been absorbed. The catalyst is removed by filtration and the solvent removed under vacuum to yield β-methyl-γ,3-dioxo-2-oxa-5-azabicyclo[2.2.1]heptane-5-butanoic acid hydroxamide.

EXAMPLE 54

β-Methyl-γ,3-dioxo-2-oxa-5-azabicyclo[2.2.1]heptane-5-butanoic acid

A mixture of 2-methyl succinic anhydride (1.2 g, 10 mmole) and cis-4-hydroxyproline lactone hydrobromide (2.1 g, 10 mmole) in pyridine (5 ml) is kept at 0° for 1 hour and allowed to warm to room temperature. After an additional hour the mixture is partitioned between ethyl acetate and 1 N HCl. The organic layer is washed with copper sulfate solution to remove traces of pyridine, dried (MgSO4) and concentrated under vacuum to yield β-methyl-γ,3-dioxo-2-oxa-5-azabicyclo[2.2.1]heptane-5-butanoic acid along with an isomer. These were separated by column chromatography.

EXAMPLES 55–60

By following the procedure of Examples 52 but substituting a compound of Column I in place of cis-4-hydroxyproline lactone hydrobromide and a compound of Column II in place of 3-carboxybutanoic acid amide, then a compound of Column III is formed.

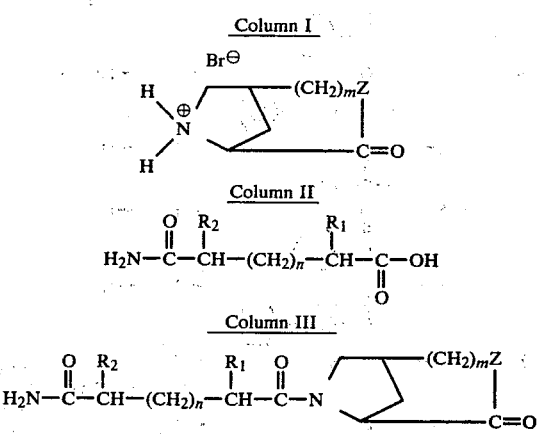

| Example | Z | R1 | R2 | n | m |
|---|---|---|---|---|---|
| 55 | —O— | —CH3 | —(CH2)2—⟨O⟩ | 1 | 0 |
| 56 | —O— | —H | —(CH2)2—⟨O⟩ | 1 | 0 |
| 57 | —NH— | —CH3 | —(CH2)2—⟨O⟩ | 1 | 0 |
| 58 | —NH— | —H | —(CH2)2—⟨O⟩ | 1 | 0 |
| 59 | —S— | —CH3 | —(CH2)2—⟨O⟩ | 1 | 0 |
| 60 | —S— | —H | —(CH2)2—⟨O⟩ | 1 | 0 |

EXAMPLES 61–66

By following the procedure of Example 53 but substituting a compound of Column I in place of cis-4-hydroxyproline lactone hydrobromide and a compound of Column II in place of 3-carboxybutanoic acid O-benzyl hydroxamide then a compound of Column III is formed.

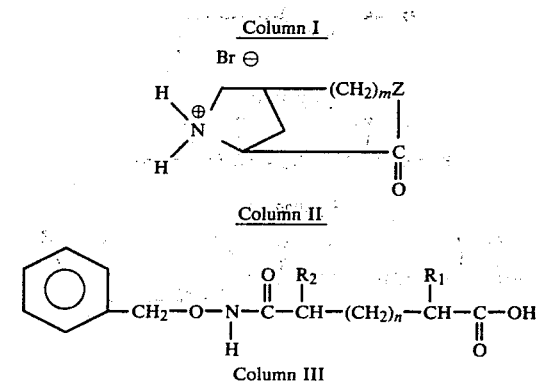

-continued

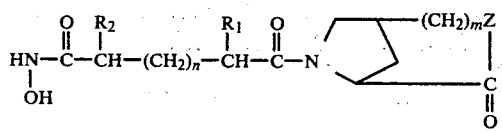

| Example | Z | R₁ | R₂ | n | m |
|---|---|---|---|---|---|
| 61 | —O— | —CH₃ | —(CH₂)₂—⌬ | 1 | 0 |
| 62 | —O— | —H | —(CH₂)₂—⌬ | 1 | 0 |
| 63 | —NH— | —CH₃ | —(CH₂)₂—⌬ | 1 | 0 |
| 64 | —NH— | —H | —(CH₂)₂—⌬ | 1 | 0 |
| 65 | —S— | —CH₃ | —(CH₂)₂—⌬ | 1 | 0 |
| 66 | —S— | —H | —(CH₂)₂—⌬ | 1 | 0 |

EXAMPLES 67–72

By following the procedure of Example 54 but substituting a compound of Column I in place of cis-4-hydroxyproline lactone hydrobromide and a compound of Column II in place of 2-methyl succinic anhydride then a compound of Column III is formed.

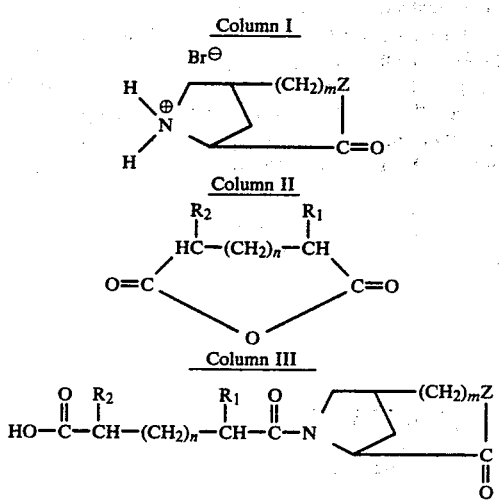

| Example | Z | R₁ | R₂ | n | m |
|---|---|---|---|---|---|
| 67 | —O— | —CH₃ | —(CH₂)₂—⌬ | 1 | 0 |
| 68 | —O— | —H | —(CH₂)₂—⌬ | 1 | 0 |
| 69 | —NH— | —CH₃ | —(CH₂)₂—⌬ | 1 | 0 |
| 70 | —NH— | —H | —(CH₂)₂—⌬ | 1 | 0 |
| 71 | —S— | —CH₃ | —(CH₂)₂—⌬ | 1 | 0 |
| 72 | —S— | —H | —(CH₂)₂—⌬ | 1 | 0 |

EXAMPLE 73

[1S-[1α,4α,5(S*)]]-5-(3-Mercapto-2-methyl-1-oxopropyl)-2-oxa-5-azabicyclo[2.2.1]heptan-2-one

[1R-[1α,4α,5(S*)]]-Ethanethioic acid, 2-methyl-3-oxo-3-(3-oxo-2-oxa-5-azabicyclo[2.2.1]hept-5-yl)-propyl S-ester (4 g) is dissolved in a mixture of water (8 ml) and concentrated ammonia (8 ml) under a blanket of nitrogen. After ten minutes stirring at room temperature, the reaction mixture is chilled, acidified and extracted with ethyl acetate. The organic layer is concentrated to dryness in vacuo to yield after purification by column chromatography [1S-[1α,4α,5(S*)]]-5-(3-mercapto-2-methyl-1-oxopropyl)-2-oxa-5-azabicyclo[2.2.1]heptan-2-one.

EXAMPLES 74–80

By following the procedure of Example 1 but substituting a compound of Column I in place of (S)-3-acetylthio-2-methylpropionyl chloride in Example 1(c) then a compound of Column II is formed. Then by substituting a compound of Column II in place of [1R-[1α,4α,5(S*)]]-ethanethioic acid, 2-methyl-3-oxo-3-(3-oxo-2-oxa-5-azabicyclo[2.2.1]hept-5-yl)propyl S-ester in Example 73 a compound of Column III is formed.

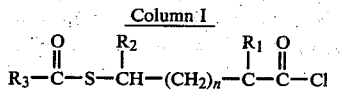

wherein R₂, R₁ and n are as defined above, and R₃ is lower alkyl.

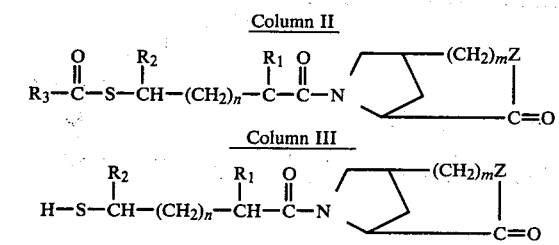

| Example | Z | R₃ | R₁ | R₂ | n | m |
|---|---|---|---|---|---|---|
| 74 | —O— | —CH₃ | —H | —(CH₂)₂—⌬ | 0 | 0 |
| 75 | —O— | —CH₃ | —CH₃ | —(CH₂)₂—⌬ | 1 | 0 |
| 76 | —O— | —CH₃ | —H | —(CH₂)₂—⌬ | 1 | 0 |

-continued

| Example | Z | R3 | R1 | R2 | n | m |
|---|---|---|---|---|---|---|
| 77 | NH | —CH3 | —CH3 | —(CH2)2—⟨O⟩ | 1 | 0 |
| 78 | NH | —CH3 | —H | —(CH2)2—⟨O⟩ | 1 | 0 |
| 79 | —S— | —CH3 | —CH3 | —(CH2)2—⟨O⟩ | 1 | 0 |
| 80 | —S— | —CH3 | —H | —(CH2)2—⟨O⟩ | 1 | 0 |

-continued

| Example | Z | R1 | R2 | n | m |
|---|---|---|---|---|---|
| 84 | NH | —CH3 | —(CH2)2—⟨O⟩ | 1 | 0 |
| 85 | NH | —H | —(CH2)2—⟨O⟩ | 1 | 0 |
| 86 | —S— | —CH3 | —(CH2)2—⟨O⟩ | 1 | 0 |
| 87 | —S— | —H | —(CH2)2—⟨O⟩ | 1 | 0 |

EXAMPLE 81

[1S-[1α,4α,5(S*)]]-5,5'-[Dithiobis(2-methyl-1-oxo-3,1-propanediyl)]bis[2-oxa-5-azabicyclo[2.2.1]heptan-3-one]

[1S-[1α,4α,5(S*)]]-5-(3-Mercapto-2-methyl-1-oxopropyl)-2-oxa-5-azabicyclo[2.2.1]heptan-2-one (1 g) is dissolved in water adjusted to pH 7 with N sodium hydroxide. An ethanolic solution of iodine is added dropwise while maintaining the pH between 6 and 7 by careful addition of N sodium hudroxide. When a permanent yellow color is obtained, the addition of iodine is stopped and the color is discharged with sodium thiosulfate. The reaction mixture is acidified and extracted with ethyl acetate. The organic layer is dried over magnesium sulfate and concentrated to dryness to yield [1S-[1α,4α,5-(S*)]]-5,5'-[Dithiobis(2-methyl-1-oxo-3,1-propanediyl)]-bis[2-oxa-5-azabicyclo[2.2.1]heptan-3-one.

EXAMPLES 82–87

By following the procedure of Example 81 but substituting a compound of Column I (made as in Examples 74–80) in place of [1S-[1α,4α,5(S*)]]-5-(3-mercapto-2-methyl-1-oxopropyl)-2-oxa-5-azabicyclo[2.2.1]heptan-2-one then a compound of Column II is formed.

EXAMPLE 88

[1S[1α,4α,5(S*)]]-5-[2-methyl-3-(methylthio)-1-oxopropyl]-2-oxa-5-azabicyclo[2.2.1]heptan-3-one (a) Methyl 3-methylthio-2-methylproponate A mixture of methyl 2-methyl-3-mercaptoproponate (1.34 g, 10 mmol) and methanol (0.42 g, 10 mmole) is added to a mixture of bis(2,2,2-trifluoroethoxy)triphenylphosphorane (11 mmole) [prepared in situ from triphenylphosphine (12 mmole) and sodium 2,2,2-trifluoroethoxide (24 mmole) in dry diethyl ether (20 ml)] in dichloromethane (20 ml). After 20 hours stirring at room temperature the mixture is poured into water and extracted with ether. The ether extract is washed with 5% aqueous sodium hydroxide and dried over magnesium sulfate. The solution is evaporated, solids removed byy filtration and the oily residue purified by vacuum distillation yielding methyl-3-methylthio-2-methylpropanoate.

(b) 3-Methylthio-2-methylpropanoic acid

A mixture of methyl-3-methylthio-2-methylpropanoate (1.48 g, 10 mmole) in tetrahydrofuran-water (50/50) (50 ml) and sodium hydroxide (0.4 g, 10 mmole) is stirred at 25° until thin layer chromatography (TLC) indicated consumption of the ester. The mixture is acidified with 1 N HCl and extracted with ether. Concentra- Column I

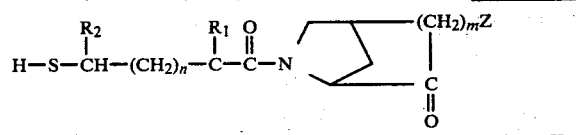

Column II

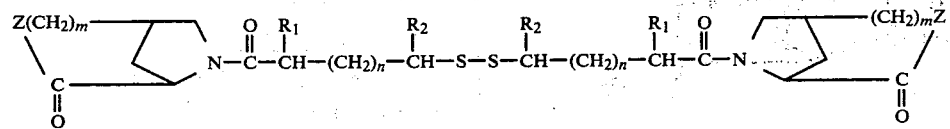

| Example | Z | R1 | R2 | n | m |
|---|---|---|---|---|---|
| 82 | —O— | —CH3 | —(CH2)2—⟨O⟩ | 1 | 0 |
| 83 | —O— | —H | —(CH2)2—⟨O⟩ | 1 | 0 | tion of the extract gives 3-methylthio-2-methylpropanoic acid.

(c) [1S]1α,4α,5(S*)]]-5-[2-methyl-3-(methylthio)-1-oxopropyl]-2-oxa-5-azabicyclo[2.2.1]heptan-3-one A mixture of 3-methylthio-2-methylpropanoic acid (1.34 g, 10 mmole) and sulfonylchloride (5 ml) is heated at reflux for 30 minutes and then concentrated to dryness under vacuum. This product is dissolved in pyridine (5 ml) and mixed with a solution of [1S]1α,4α)-2-oxa-5-azabicyclo[2.2.1]heptane-3-one hydrobromide (1.93 g, 10 mmole) and the mixture stirred at 25° C. until thin layer chromatography (TLC) showed consumption of starting material. The pyridine is removed under vacuum and the residue partitioned between ether and 1 N HCl. The ether layer is dried (MgSO4) and concentrated yielding [1S[1α,4α,5(S*)]]-4-[2-methyl-3-(methylthio)-1-oxopropyl]2-oxa-5-azabicyclo[2.2.1]-heptan-3-one which is purified by column chromatography.

EXAMPLES 89-94

By following the procedure of Example 88 but substituting a compound of Column I in place of methyl 2-methyl-3-mercapto-propanoate and a compound of Column II in place of methanol and a compound of Column III in place of [1S[1α,4α]-2-oxa-5-azabicyclo[2.2.1)heptan-3-one a compound of formula IV is obtained.

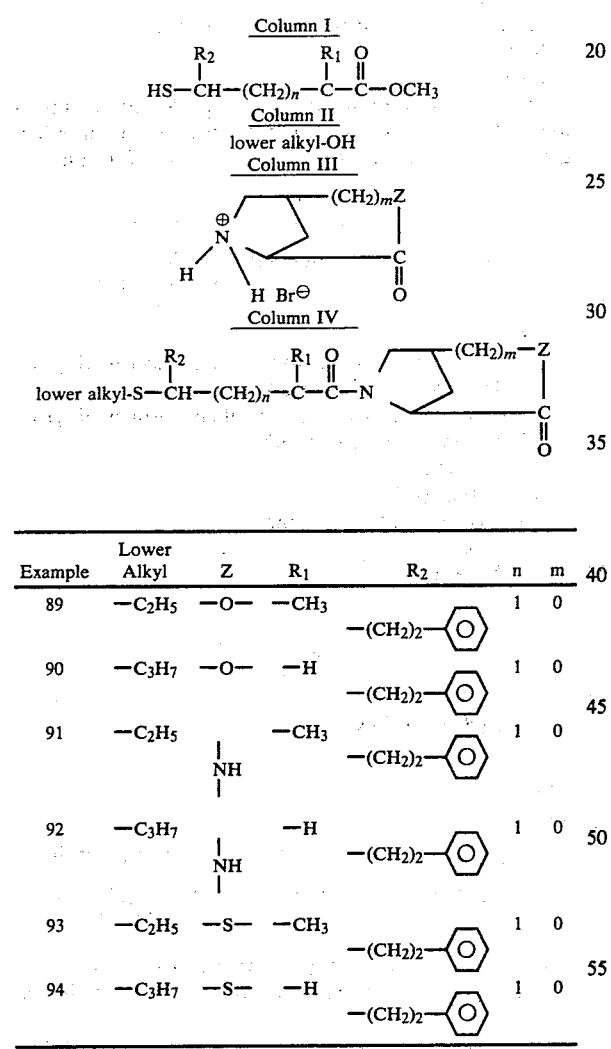

EXAMPLE 95-102

By following the procedure of Example 4 (a-c) but substituting a compound of Column I in place of H-benzoyl oxycarbonyl-4-trans-hydroxyproline in part (a) to obtain a compound of Column II, then following the procedure of Example 1(c) but substituting the compound of Column II in place of cis-4-hydroxy-L-proline lactone HBr salt and a compound of Column III in place of (S)-3-acetylthio-2-methylpropionyl chloride, then a compound of Column IV is formed.

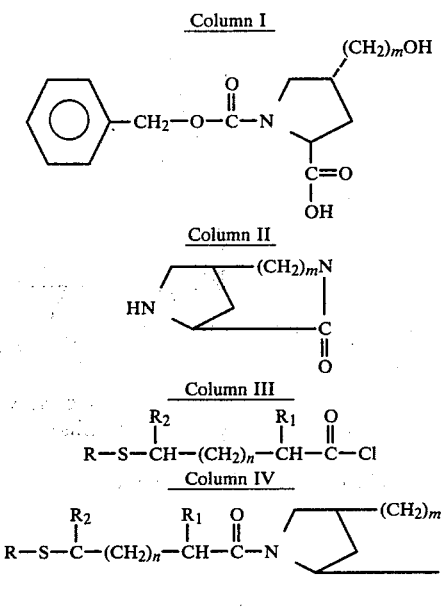

| Example | R | R₁ | R₂ | n | m |
|---|---|---|---|---|---|
| 95 | $-\overset{O}{\underset{\|}{C}}-CH_3$ | —H | $-(CH_2)_2-\text{Ph}$ | 1 | 0 |
| 96 | $-\overset{O}{\underset{\|}{C}}-\text{Ph}$ | —H | $-(CH_2)_2-\text{Ph}$ | 1 | 0 |
| 97 | $-\overset{O}{\underset{\|}{C}}-CH_2-\text{Ph}$ | —H | $-(CH_2)_2-\text{Ph}$ | 1 | 0 |
| 98 | $-\overset{O}{\underset{\|}{C}}-CH_3$ | —CH₃ | $-(CH_2)_2-\text{Ph}$ | 1 | 0 |
| 99 | $-\overset{O}{\underset{\|}{C}}-\text{Ph}$ | —CH₃ | $-(CH_2)_2-\text{Ph}$ | 1 | 0 |
| 100 | $-\overset{O}{\underset{\|}{C}}-CH_2-\text{Ph}$ | —CH₃ | $-(CH_2)_2-\text{Ph}$ | 1 | 0 |
| 101 | —CH₃ | —H | $-(CH_2)_2-\text{Ph}$ | 1 | 0 |
| 102 | —C₂H₅ | —H | $-(CH_2)_2-\text{Ph}$ | 1 | 0 |

What is claimed is:

1. A compound of the formula

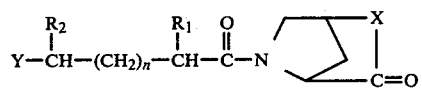

wherein

R₁ is hydrogen, lower alkyl, phenyl lower alkyl or halo substituted lower alkyl;

R₂ is hydrogen, lower alkyl, phenyl lower alkyl or halo substituted lower alkyl;

n is 0, 1 or 2;

X is —(CH$_2$)$_m$Z—;
Z is oxygen, sulfur or imino;
m is 0 or 1;
Y is S—R or

R is hydrogen, lower alkyl,

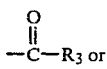

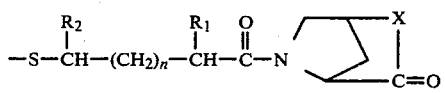

R$_3$ is lower alkyl, phenyl or phenyl lower alkyl;
and R$_4$ is hydroxy, amino, hydroxyamino or lower alkoxy.

2. The compound of claim 1 wherein
Y is S—R;
R is

R$_3$ is lower alkyl,
R$_2$ is phenyl lower alkyl or hydrogen;
R$_1$ is lower alkyl;
n is 1;
m is 0;
and Z is oxygen.

3. The compound of claim 1 wherein
Y is

R$_4$ is lower alkoxy
R$_2$ is phenyl lower alkyl or hydrogen;
R$_1$ is lower alkyl;
n is 1;
m is 0;
and Z is oxygen.

4. The compound of claim 1 wherein
Y is S—R;
R is

R$_3$ is lower alkyl;
R$_2$ is phenyl lower alkyl or hydrogen;
R$_1$ is lower alkyl;
n is 0;
m is 0;
and Z is oxygen.

5. The compound of claim 1 wherein
Y is

R$_4$ is lower alkoxy;
R$_2$ is phenyl lower alkyl or hydrogen;
R$_1$ is lower alkyl;
n is 0;
m is 0;
and Z is oxygen.

6. The compound of claim 4 wherein [1R-[1α-4α,5(S*)]]-ethanethioic acid, 2-methyl-3-oxo-3-(3-oxo-2-oxa-5-azabicyclo[2.2.1]hept-5-yl)propyl S-ester.

7. The compound of claim 2 wherein
R$_1$ is methyl and
R$_2$ is phenylethyl or hydrogen.

8. The compound of claim 2 wherein
R$_1$ is methyl and
R$_2$ is hydrogen.

9. The compound of claim 3 wherein
R$_1$ is methyl and
R$_2$ is phenylethyl.

10. The compound of claim 3 wherein
R$_1$ is methyl and
R$_2$ is hydrogen.

11. A composition for treating hypertension comprising a pharmaceutically acceptable carrier and an effective amount of a hypotensive agent of the formula

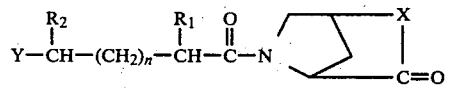

wherein
R$_1$ is hydrogen, lower alkyl, phenyl lower alkyl or halo substituted lower alkyl;
R$_2$ is hydrogen, lower alkyl, phenyl lower alkyl or halo substituted lower alkyl;
n is 0, 1 or 2;
X is —(CH$_2$)$_m$Z—;
Z is oxygen, sulfur or imino;
m is 0 or 1;
Y is S—R or

R is hydrogen, lower alkyl,

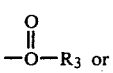

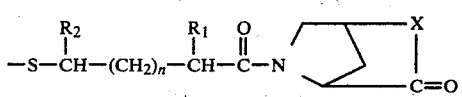

R$_3$ is lower alkyl, phenyl or phenyl lower alkyl;
and R$_4$ is hydroxy, amino, hydroxyamino or lower alkoxy.

12. The composition of claim 11 also including a diuretic.

13. The method of alleviating hypertension which comprises administering an effective amount of the composition of claim 11.

14. The compound of claim 1 wherein
Y is S—R;
R is hydrogen;
R$_2$ is phenyl lower alkyl or hydrogen;
R$_1$ is lower alkyl;

n is 1; m is zero and Z is oxygen.

15. The compound of claim 1 wherein

Y is S—R;

R is hydrogen;

$R_2$ is phenyl lower alkyl or hydrogen;

$R_1$ is lower alkyl;

n is 0; m is 0 and Z is oxygen.

* * * * *

UNITED STATES PATENT OFFICE
CERTIFICATE OF CORRECTION

PATENT NO. : 4,303,662
DATED : December 1, 1981
INVENTOR(S) : Peter W. Sprague

It is certified that error appears in the above-identified patent and that said Letters Patent are hereby corrected as shown below:

Col. 7, line 55, delete "[1R-[1α, 5(S*)]]-" and insert -- [1R-[1α,4α,5(S*)]]- --.
Col. 24, line 50 the formula should read

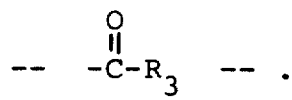

-- $-\overset{\overset{O}{\|}}{C}-R_3$ --.

Signed and Sealed this

Sixteenth Day of November 1982

[SEAL]

Attest:

GERALD J. MOSSINGHOFF

Attesting Officer    Commissioner of Patents and Trademarks